United States Patent
Hubbard et al.

(10) Patent No.: US 7,204,947 B2
(45) Date of Patent: Apr. 17, 2007

(54) METHOD OF CROSSLINKING POLYOLEFINS

(75) Inventors: Neil Trevor Hubbard, Burnley (GB); Cherryl Ann Cooper, Wigan (GB)

(73) Assignee: Orthoplastics Limited, Lancashire (GB)

( * ) Notice: Subject to any disclaimer, the term of this patent is extended or adjusted under 35 U.S.C. 154(b) by 13 days.

(21) Appl. No.: 10/956,188

(22) Filed: Sep. 30, 2004

(65) Prior Publication Data

US 2005/0070625 A1    Mar. 31, 2005

Related U.S. Application Data

(63) Continuation of application No. 10/243,636, filed on Sep. 12, 2002, now abandoned.

(30) Foreign Application Priority Data

Sep. 13, 2001  (GB) .................................... 0122117

(51) Int. Cl.
  *A61F 2/02*   (2006.01)
  *B29B 11/14*  (2006.01)
  *B29B 13/08*  (2006.01)
(52) U.S. Cl. ................. 264/239; 264/331.17; 264/494; 522/161; 522/157
(58) Field of Classification Search ............... 264/239, 264/331.17, 494; 522/161, 157
See application file for complete search history.

(56) References Cited

U.S. PATENT DOCUMENTS

| 3,644,186 | A | * | 2/1972 | Gracia et al. ............... 522/159 |
| 4,743,258 | A | * | 5/1988 | Ikada et al. ................ 623/1.49 |
| 4,797,438 | A |   | 1/1989 | Kletecka et al. |
| 5,414,049 | A | * | 5/1995 | Sun et al. ................ 525/333.7 |
| 5,879,400 | A |   | 3/1999 | Merrill et al. |
| 6,017,975 | A |   | 1/2000 | Saum et al. |
| 6,281,264 | B1 | * | 8/2001 | Salovey et al. ............. 523/115 |
| 6,328,923 | B1 | * | 12/2001 | Jones et al. ................ 264/494 |

FOREIGN PATENT DOCUMENTS

| EP | 0722973 A1 | 7/1996 |
| WO | WO 97/29793 | 8/1997 |
| WO | WO 98/01085 | 1/1998 |

OTHER PUBLICATIONS

European Search Report in Corresponding EP application 02256351.4.

* cited by examiner

*Primary Examiner*—Susan Berman
(74) *Attorney, Agent, or Firm*—Beyer Weaver LLP

(57) ABSTRACT

A method of forming an engineering component comprising the steps of:
  subjecting a workpiece or blank formed from polyolefin to gamma radiation at a total dose sufficient to cause a predetermined degree of crosslinking, wherein the total dose is applied at a dosage rate of less than 5 kGy/hour to cause crosslinking of the polymer and forming an engineering component from the crosslinked material.

5 Claims, No Drawings

METHOD OF CROSSLINKING POLYOLEFINS

This is a continuation of Application Ser. No. 10/243,636 filed Sep. 12, 2002 now abandoned, which is incorporated herein by reference.

This invention relates to the method of crosslinking polyolefins, particularly but not exclusively polyethylene using gamma radiation. Cross-linking is beneficial as it improves the wear resistance of polyethylene used in orthopaedic implants and other engineering applications, especially ultra-high molecular weight polyethylene (UHMWPE) used for these applications.

The crosslink density, that is the distance between bonds, is proportional to the radiation dose received. Wear resistance increases with higher crosslink density that occurs following use of higher doses of radiation. The detrimental counter effect of crosslinking is to reduce many mechanical and physical properties of the polymer. This reduction also occurs in proportion to the dose received. Higher doses cause greater reduction in physical properties. A reduction in strength may lead to a physical failure of the component. The maximum dose, and hence the maximum enhancement of wear that can be used in a particular circumstance is limited by this reduction in other physical properties. Commercial highly crosslinked UHMWPE has previously been treated with a specified total gamma radiation dose. The actual dose rate has not been considered important and has generally been left to the convenience of a vendor or contractor. Typically the crosslinking of polyethylene has been carried out at a dose rate of about 5 kilo Gray (kGy) per hour or higher (0.5 MRad/h).

Accordingly to the present invention a method of forming an engineering component comprises the steps of:

subjecting a workpiece or blank formed from polyolefin to gamma radiation at a total dose sufficient to cause a predetermined degree of crosslinking, wherein the total dose is applied at a dosage rate of less than 5 kGy/hour to cause crosslinking of the polymer and forming an engineering component from the crosslinked material.

In a preferred method the dosage rate is less than 3 kGy/hour, more preferably less than 1.5 kGy/hour.

The dosage time is adjusted to provide a sufficient total dosage to cause efficient crosslinking and sterilisation. The total dosage may be selected by conventional means. A common total dose of 100 k Gy may be used, although doses from 40 kGy to more than 102 kGy may be used for UHMWPE for orthopaedic prostheses and implants.

By reducing the dose rate to below 5 kGy/hour, preferably below 3 kGy/hour and most preferably below 1.5 kGy/hour, there is a significant improvement in the mechanical properties, particularly the crystallinity, impact strength and elongation at break. Conventional cross-linking by irradiation at higher dosage rates may decrease the crystallinity of UHMWPE from 50% to 35% for a total dose of 100 kGy. The use of the lower dose rate in accordance with this invention can maintain a level of crystallinity over 40%, leading to a consequent reduction in the loss of impact strength and elongation at break; The loss of these mechanical properties has been found to be less at lower dose rates for the same total dose level.

The polyolefin is preferably a polyalphaolefin, preferably selected from polyethlene, polypropylene and copolymers and blends thereof. Use of ultra high molecular weight polyethylene with molecular weight >$1\times10^6$ g/mol preferably >$3\times10^6$ g/mol is especially preferred.

The invention is further described by means of example but not in any limitative sense.

EXAMPLE 1

Ultrahigh molecular weight polyethylene (UHMWPE) was crosslinked by gamma radiation from a cobalt 60 source at four different dose rates to the same total dose (100 kGy). The dose was assessed by dosimeters in accordance with BS EN 552. The exercise was repeated to provide 3 sets of test materials.

The degree of crosslinking (cross-link density) was measured using a SRT 1 (Swell Ratio Tester) supplied by Cambridge Polymer Group of Sommerville Mass., USA to the draft ASTM standard D2765[1] in accordance with the procedure used for the round robin tests. The four samples within each set were the same (no significant difference) thus demonstrating the same crosslink density and no effect of dose rate.

Mechanical and physical properties were measured in accordance with the standards stated in Table 1 and the results analysed using Student's t test for matched pairs to demonstrate significance.

The dose rate was demonstrated to have a significant effect on the Impact Strength, Elongation at break and Crystallinity. Lower dose rates provided materials with significantly better properties than those produced at high dose rates.

TABLE 1

| Method | Dose Rate kGy/hr Calculation | Swell Ratio | Crosslink Density ASTM D2765[2] | Crystallinity % D.S.C[3] | Impact Strength kJ/m$^2$ Izod[4] | Elongation % ASTM F 648 |
|---|---|---|---|---|---|---|
| DR1 | 1.0 | 3.1 | 0.15 | 42.3 | 63 | 239 |
| DR2 | 1.8 | 3.0 | 0.16 | 38.3 | 62 | 235 |
| DR3 | 6.1 | 3.0 | 0.165 | 36.7 | 58 | 234 |
| DR4 | 7.3 | 3.1 | 0.155 | 34.4 | 59 | 224 |

[1]Student's Test P = <0.05
[2]Draft 3.2, March 2001
[3]Differential Scanning Calorimeter
[4]ASTM F648-00

EXAMPLE 2

Orthopaedic grade, ram extruded GUR 1050 rods of 65 mm diameter were manufactured from gamma irradiation in air to a dose level of 100 kGy. Mapping of the irradiation plant was carried out using dosimetry to determine the placement of rods to achieve the specified nominal dose rates. Each set of four rods were irradiated at different nominal dose rates of 1, 2, 6, and 7.5 kGy per hour.

TABLE 2

| Nominal Dose rate kGy/hr | Actual Dose Rate kGy/hr | Dose Level KGy EN 552 | Range kGy |
|---|---|---|---|
| 1.0 | 1.0 | 99.9–101.4 | 1.5 |
| 2.0 | 1.8 | 97.7–100.8 | 3.1 |
| 6.0 | 6.1 | 95.8–102.7 | 6.9 |
| 7.5 | 7.3 | 96.3–104.8 | 8.5 |

The rods were melt annealed in an air atmosphere at 150 C with a slow cool down rate to ambient temperature. The rods were machined into test specimens with a minimum sample size of six for each dose rate. Tensile Strength, Yield Strength and Elongation at Break were determined in accordance with ISO 527 using Type 5 specimens. Impact Strength testing conformed to ASTM F648-00 Annex A1 using double notch Izod specimens. Cross-link density and swell ratio was determined using the SRT-1 (Cambridge Polymer Group) to the draft ASTM standard 3.2 Mar. 1, 2001. Samples of 150 μm were tested on a Nicolet FTIR with microscope to determine the Transvinyl Index (TVI) (Muratoglu, O. K. et al., 47$^{th}$ ORS 2001 p. 1013) and a Netsch Differential Scanning Calorimeter to determine the crystallinity. Gamma irradiation using the above mentioned dose rates and testing was carried out on three independently crosslinked sample sets. Statistical analysis was performed using Graphpad software and a p-value <0.05 was used to establish significance. A comparison was made to rods irradiated during a production run of two hundred rods of the same diameter and dose level, but using a dose rate of 0.4 kGy per hour.

TABLE 3

| | Radiation Rate in kGy/Hour | | | | |
|---|---|---|---|---|---|
| Property | 0.4 | 1.0 | 1.8 | 6.1 | 7.3 |
| Impact Strength kJ/m$^2$ | 64 | 63 | 62 | 59 | 59 |
| Yield Strength MPa | 20.4 | 19.6 | 19.5 | 19.4 | 19.3 |

TABLE 3-continued

| | Radiation Rate in kGy/Hour | | | | |
|---|---|---|---|---|---|
| Property | 0.4 | 1.0 | 1.8 | 6.1 | 7.3 |
| Tensile Strength MPa | 44.2 | 43.2 | 41.3 | 41.1 | 42.8 |
| Elongation at break % | 246 | 239 | 236 | 234 | 224 |
| Swell Ratio | 3.04 | 3.14 | 3.00 | 2.97 | 3.06 |
| Cross-link Density Mole/dm$^3$ | 0.16 | 0.15 | 0.16 | 0.16 | 0.16 |
| Crystallinity % | 43.0 | 42.3 | 38.3 | 36.7 | 33.9 |

Izod impact strength, elongation at break, yield strength and crystallinity showed a significant decrease with increasing dose rate (p<0.05). The square of the correlation coefficient ($R^1$) for yield strength versus crystallinity was 0.9985. The square of the correlation coefficient ($R^1$) for Izod impact strength versus dose rate was 0.9998. The level of crystallinity reduced by 20% with increase dose rate whilst swell ratio and cross-link density showed no statistical significance between dose rate.

The invention claimed is:

1. A method of forming an engineering component comprising the steps of:
    subjecting a workpiece or blank formed from ultra high molecular weight polyethylene to gamma radiation at a total dose of about 100 kGy sufficient to cause a predetermined degree of crosslinking, wherein the total dose is applied at a dosage rate of less than 1.0 kGyA/hour to cause crosslinking of the polymer and forming an engineering component from the crosslinked material.

2. A method as claimed in claim 1 wherein the dosage rate is less than 0.4 kGy/hour.

3. A method as claimed in claim 1 wherein the crystallinity of the crosslinked ultra high molecular weight polyethylene is at least 40%.

4. An engineering component comprising ultra high molecular weight polyethylene crosslinked in accordance with claim 1.

5. A surgical implant or prostheses comprising a ultra high molecular weight polyethylene crosslinked in accordance with the method of claim 1.

* * * * *